United States Patent [19]

Falk et al.

[11] Patent Number: 5,014,561
[45] Date of Patent: May 14, 1991

[54] METHOD AND APPARATUS FOR OBTAINING ACCURATE SAMPLE

[75] Inventors: Richard A. Falk, Ft. Lauderdale, Fla.; Larry Janicsek, Waukesha, Wis.; Joseph Boron, Medina, Ohio; James Colzani, Menomonee Falls, Wis.

[73] Assignee: Midwest Instrument Co., Inc., Hartland, Wis.

[21] Appl. No.: 359,849

[22] Filed: May 31, 1989

[51] Int. Cl.⁵ ............................................... G01N 1/12
[52] U.S. Cl. ............................ 73/864.53; 73/863.11; 73/864.58
[58] Field of Search ........................ 73/864.53–864.59, 73/DIG. 9, 863.11

[56] References Cited

U.S. PATENT DOCUMENTS

| 2,485,492 | 10/1949 | Hubbard et al. | 73/DIG. 9 X |
|---|---|---|---|
| 3,221,559 | 12/1965 | Miller, Jr. et al. | 73/DIG. 9 X |
| 3,534,614 | 10/1970 | Croswell | 73/864.58 X |
| 3,565,606 | 2/1971 | Carlson et al. | 73/DIG. 9 X |
| 3,748,908 | 7/1973 | Falk | 374/26 |
| 3,791,219 | 2/1974 | Falk | 73/864.57 |
| 3,905,238 | 9/1975 | Falk | 73/864.54 |
| 4,069,715 | 1/1978 | Falk | 73/864.59 X |
| 4,069,717 | 1/1978 | Falk | 73/864.56 |
| 4,659,679 | 4/1987 | Falk | 106/84 X |
| 4,815,326 | 3/1989 | Falk | 73/864.53 |

FOREIGN PATENT DOCUMENTS

| 2462699 | 3/1981 | France | 73/864.53 |
|---|---|---|---|
| 429308 | 10/1974 | U.S.S.R. | 73/864.53 |
| 1460024 | 12/1976 | United Kingdom | 73/864.53 |

Primary Examiner—Tom Noland
Attorney, Agent, or Firm—Fuller, Ryan & Hohenfeldt

[57] ABSTRACT

Method and sampling apparatus for obtaining accurate carbon samples in ultra-low carbon melts includes a capping system for the fill tube which uses Pyrex or low carbon steel caps, preheating or preigniting parts to burn off contaminants and a zircon coating can be employed around the immersion vehicle to prevent carbon contaminants from reaching the sample mold.

13 Claims, 1 Drawing Sheet

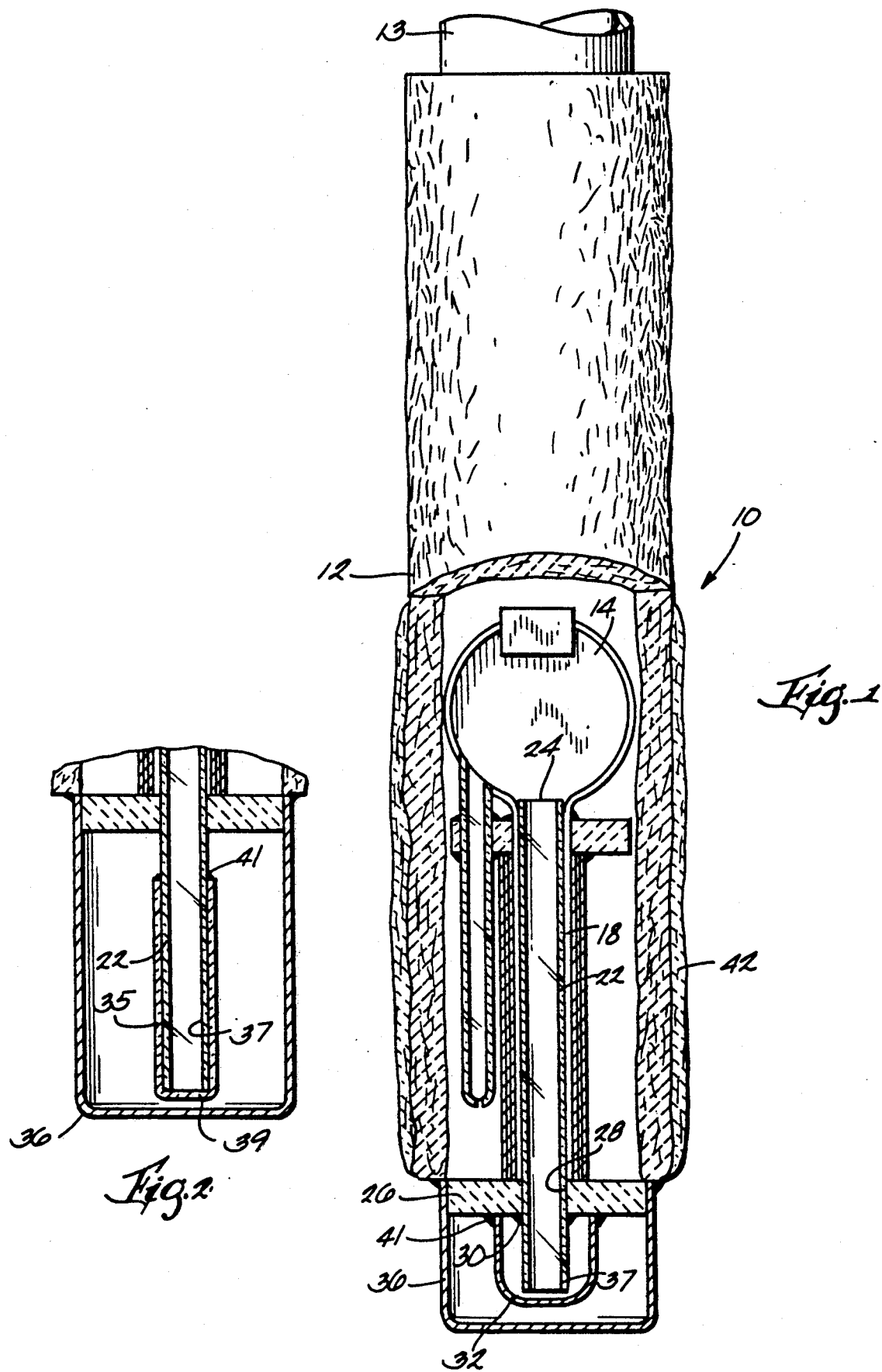

METHOD AND APPARATUS FOR OBTAINING ACCURATE SAMPLE

FIELD OF THE INVENTION

The invention relates to molten metal samplers for retrieving samples for laboratory analysis.

BACKGROUND OF THE INVENTION

A field of steel making has developed in which there is a demand for ultra-low carbon steel of 0.01% carbon or less. Conventional molten metal samplers have too many contaminants to be useful for sampling the melts during the steel making process to determine the composition of the melt. We have discovered various sources of carbon contamination that can affect and distort the lab analysis. Conventional samplers of the type shown in U.S. Pat. Nos. 3,791,219 and 4,069,715 are effective in other than ultra-low carbon melts. However, samplers of this type are not adequate to provide the desired accuracy free of distortion in ultra-low carbon steel melts.

SUMMARY OF THE INVENTION

The invention provides a method and apparatus for sampling ultra-low carbon steel to give reliable and consistent analysis which are of use in the manufacture of such steel. Various of the sampler parts are selected to avoid contamination. The immersion vehicle can be made of rice hulls mixed with refractory fiber in accordance with U.S. Pat. No. 4,659,679, the entire disclosure of which is incorporated herein by reference. The metal stampings used to define the mold cavity can be cleaned with a solvent such as carbon tetrachloride to remove lubricant used in the presses which can contain from 1.0% to 5.0% carbon and sulfur. The stampings can also be preheated or burned in a high temperature inert gas or vacuum oven.

The quartz fill tube for conveying molten metal from the exterior into the mold parts can be heated to burn off the grease that accumulates on the exterior of the tube during manual handling of the same.

To prevent entry of contaminants into the mold cavity the capping system is selected for the fill tube to prevent entry of contaminants into the sample mold. A double capping system is employed such as that shown in FIG. 4 of U.S. Pat. No. 4,069,715 with an inner cap 49 and an outer cap 53. In U.S. Pat. No. 4,069,715 the cap 49 was typically made of metal. The present invention provides an elongated Pyrex cap with a sealed end which encloses the end of the fill tube and fits tight against the fill tube. The Pyrex cap 15 is cemented in place a significant distance from the entrance to the fill tube with an aluminum silicate cement. The cement seal is located remotely from the tip of the fill tube so that the cement will not be washed into the fill tube and then the sample cavity. A cement is also used which has no significant carbon contaminants. Alternatively, a low carbon steel inner cap could be employed rather than the Pyrex.

In the prior art samplers the outer slag caps are sometimes painted. This was found to be one source of carbon contamination. Accordingly, the large outer slag cap is made from a low carbon steel, close in carbon content to the steel melt being sampled so that the sample analysis is not distorted.

The immersion vehicle is also provided with a coating of zircon flour which is water based and ethyl alcohol added to reduce surface tension. The zirconium coating provides a seal of the rice hull jacket for a substantial distance from the fill tube to prevent any carbon contaminants from the jacket reaching the fill tube during immersion and recovery of a sample.

Further objects, advantages and features of the invention will become apparent from the disclosure.

DESCRIPTION OF THE DRAWINGS

FIG. 1 is a side elevational view of a sampler in accordance with the invention; and FIG. 2 is a view of an alternative embodiment of the cap assembly.

DESCRIPTION OF A PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

The sampling lance 10 includes an immersion vehicle 12 which can be formed from any low carbon non boiling sleeve which can be supported by a pipe 13. In the disclosed construction, the immersion vehicle is a preformed sleeve made from rice hull ash as disclosed in my U.S. Pat. No. 4,659,679. A common immersion vehicle used in general sampling is the paperboard sleeve illustrated in my U.S. Pat. No. 3,791,219. Paperboard sleeves provide relatively long immersion lives due to the combustion and gassing of the paperboard during combustion in the melt which gassing acts as an insulator. However, we have discovered that the burning of the paperboard is a source of carbon in the melt and accordingly paperboard, is not appropriate for support of the mold cavity when sampling ultra low carbon steel melts. The mold cavity 14 is defined by clam shell mold halves such as that shown in FIG. 3 of my U.S. Pat. No. 3,791,219, the entire disclosure of which is incorporated by reference. The mold halves can be made of steel or refractory and have steel extension parts 18 which clamp around and provide support for a fused quartz inlet tube 22 which communicates at an outlet 24 with the cavity 14. The fill tube can be supported by a refractory disk 26 which has an aperture 28 which tightly receives the tube. The tube can be sealed to the disk 26 by a bead of cement 30. Refractory alumina silicate cement called Blome 19 made by Blome Cement Co., St. Louis, MO has been found suitable. It has been found that some of the glues or adhesives previously used in samplers had a significantly high carbon content which can contaminate the sample.

The invention provides a capping system for the inlet tube 22. An inner slag cap 32 is employed to prevent entry of slag prior to reaching an immersion depth beneath the slag. The cap 32 can be of Pyrex (trademark of Corning) or low carbon steel having a carbon content close to the steel melt being sampled. If Pyrex is used it will induce silicon and boron impurities. However these impurities are not of concern in low carbon sampling. Pyrex has a lower melting point than the fused quartz tube. A single Pyrex cap can be employed.

FIG. 2 shows a modified embodiment of a capping system wherein the inlet tube 22 is provided with an elongated Pyrex cap 35. The cap 35 has a diameter close to but slightly larger than the fill tube 22. The tip 37 of the fill tube is close to the end 39 of the cap 35. This is believed to minimize the contaminants from entering the fill tube from the sampler cap, parts, etc. and slag. The outer tube 35 is cemented at the end 41 to the fill tube 22. End 41 is located remotely from the fill tube end 37 to minimize contaminants and cement from entering the fill tube 22.

The outer slag cap 36 is selected from a metal having similar carbon content to the steel melt being sampled to avoid contamination because the melted cap portions are likely to enter the sampler with the rush of metal from the melt caused by the ferrostatic pressure of the column of metal above the inlet tube. The FIG. 1 embodiment would also use a low carbon steel cap 36.

To prevent entry of carbon from the immersion vehicle which supports the mold halves, a coating 42 is applied for several inches from the end of the immersion vehicle along the cylindrical side wall. The coating 42 is water based zircon flour. Zircon is a mineral which is zirconium orthosilicate. This prevents any contaminants from the rice hull ash getting into the entrance of the fill tube. A zircon coating of up to six inches or longer on the wall of the immersion vehicle extending upwardly from the lower end of the paperboard or rice hull ash immersion vehicle provides adequate protection from carbon in the immersion vehicle sleeve.

Although the sampler shown is an immersion type sampler, the invention disclosed herein can be used in other types of sampling devices such as those shown in U.S. Pat. Nos. 4,503,716 and 4,699,014 and sucker samplers such as that shown in U.S. Pat. Nos. 3,748,908 and 3,996,803, stream samplers such as that illustrated in U.S. Pat. No. 4,069,717 and a sucker sampler as shown in U.S. Pat. No. 3,905,238. Evacuated samplers such as that shown in U.S. Pat. No. 4,815,326 can be employed. The entire disclosure of each of these patents is incorporated herein by reference. Applying the invention to these samplers and others would involve use of a capping system as described, no carbon cement and a protective coating over the immersion vehicle sleeve.

Tables I, II, III, and IV show various tests which demonstrate the advantages and accuracy of the invention for low carbon measurements. Table I, the Minco ULC Sucker Sampler is the low carbon sampler of the invention. It was compared with tests performed by other samplers and then compared with a sample taken from the actual slab caster. The results are within one or two ten-thousandths percent carbon. The other tables demonstrate other comparisons to show the accuracy of the sampler.

All the samples in the test sample were subjected to combustion analysis in a LECO combustion analyzer excerpt where noted.

TABLE I

COMPARATIVE SAMPLER DATA

Three different samplers from slab caster mold.
Test Data. Slab Caster mold fed by BOF furnaces. Hand immersed samplers. Tests were conduced at an internationally-known, multi-plant steelmaker.
Tests on four heats for Carbon %.

| Regular Production Sucker Sampler Supplied by worldwide sampler manufacturer | Special evacuated pin test - Japanese origin supplied by worldwide sampler manufacturer | Minco ULC Sucker sampler | Slab Check |
|---|---|---|---|
| — | — % C. | .0022 | .0023 |
| .0050% C. | .0059 | .0015 | .0017 |
| — | .0092 | .0020 | .0020 |
| — | .0037 | .0023 | .0021 |

The Minco ULC Sucker Sampler employed was made in accordance with U.S. Pat. No. 3,905,238 and employed a Pyrex cap secured with Blome 19 cement. The metal mold parts were degassed in a vacuum oven. The slab check was made by removing a portion of metal from the slab after it solidified. The tests show that the Minco sample had test results identical or very close to the slab measurements, demonstrating the success of the special capping system of FIG. 2.

TABLE II

COMPARATIVE SAMPLER DATA

A - 6 IMMERSIONS
B - 13 IMMERSIONS
All 19 immersions from one heat - Tundish - comparing drillings from dual thickness sampler ⅛" body to punchings from 4 mm duckbill. Immersion system mechanical. Internationally known BOF steelmaker.
A. Minco ULC sampler - 6 immersions - 1 ladle
  Average % Carbon from drillings from sampler body .00535% C.
  Max Deviation +/− .00005 in all samples
  Average % Carbon from punched pellets from duckbill .0054% C.
  Max Deviation +/− .0002
  Average 3 slab tests .00573
  Max Deviation +/− .0002
B. Regular Dual Thickness Sampler Competition duckbill - 13 immersions - 1 heat - Tundish
  Average % Carbon from drillings from sampler body .0081
  Max Deviation +/− .0013
  Average % Carbon from punched pellets from duckbill .01125
  Max Deviation +/− .0023
  Average 3 slab tests .00573
  Max Deviation +/− .0002

Conclusion: ⅛ of sampler introduced impurities are deposited in the thin rear duckbill of the competitors dual thickness sampler.

The Minco ULC sampler used in Test A was similar to that shown in U.S. Pat. No. 4,815,326, FIG. 4 with rice-hull fiber jacket coating and a capping system in accordance with those described herein. The entire disclosure of U.S. Pat. No. 4,815,326 is incorporated herein by reference. Drillings were obtained from the thick sample portion and stampings from the thin portion.

The sampler in Test B was a sample similar to a competitors "duckbill" with a disc and thin web similar to the sample shown in FIG. 1 of U.S. Pat. No. 4,503,716. The test results of A show that the Minco ULC sampler had consistent results between samples taken from the thin and thick portions. The test results of B show some contamination because of the large differences in carbon measurements between the thin and thick portions.

TABLE III
COMPARATIVE SAMPLE DATA IMMERSION DEGASSER TESTS

Ladle fed by BOF. Samples by Hand Immersion. Internationally-known, multi-plant steelmaker. 4 heats tested.

| Regular Immersion Test By Sampler Manufacturer Who Markets Internationally | Minco ULC Immersion Sampler | Minco ULC Sucker Sampler Tundish Sampler | Slab Check |
| --- | --- | --- | --- |
| 0.10% C. | .003% | .004% | .004% C. |
| .008 | .004 | .006 | .005 |
| .008 | .003 | .006 | .005 |
| .015 | .004 | .004 | .004 |

The Minco ULC immersion sampler was similar to that shown in U.S. Pat. No. 4,815,326 with the mold halves degassed in a vacuum oven and with a low carbon outer metal cap and a Pyrex inner cap. The Minco Sucker sampler was degassed in a vacuum oven. It employed a Pyrex cap secured with Blome 19 cement.

The test results show that the Minco samplers made in accordance with the invention compared very closely with the slab check. The competitor's sampler provided sample results significantly different from the slab checks.

TABLE IV
COMPARATIVE PRECISION TESTS BY IMMERSION FROM DEGASSER

Hand Immersion. Internationally known Steelmaker. BOF Fed Degasser. 4 Heats Tested.

| Regular Immersion Test | Minco ULC Test Type 1 | Type 2 | OFS Special Pin Test Evacuated | Special Referee Test |
| --- | --- | --- | --- | --- |
| .0088% C. | .0029% C. | .0027% C. | .0033% C. | .0026% C. |
| .0073 | .0038 | .0034 | .0041 | .0044 |
| .0064 | .0028 | .0027 | .0057 | .0037 |
| .0050 | .0013 | .0012 | .0025 | .0013 |

The special pin test evacuated sampler is made in accordance with U.S. Pat. No. 4,815,326 but with the contaminant avoidance teachings disclosed herein.

The Minco ULC Test sampler was similar to that shown in FIG. 1 and had mold halves degassed in a vacuum oven, a rice hull jacket as the immersion vehicle, and a Pyrex inner cap and a low carbon metal outer cap.

We claim:

1. A method for obtaining an accurate low carbon reading from a steel melt comprising the steps of:
   providing a sampler including sample mold parts which are de-contaminated prior to assembly to drive off impurities and providing a fused quartz fill tube to introduce a sample into the sample mold which fill tube is pre-ignited prior to assembly to remove impurities and surface contamination;
   providing a low carbon cap for the fill tube, the cap having a carbon content approximate to the carbon content of the bath being sampled and said mold having an immersion vehicle including a carbon free coating to prevent the formation of carbon or carbon dioxide during immersion of the sampler in the molten metal in a zone around the fill tube entrance,
   removing the sample from sampler, cleaning the surface to remove contamination and obtaining a sample from the cast sample for analysis.

2. The method of claim 1 wherein the step of de-contaminating the mold parts includes heating the parts in a vacuum furnace.

3. The method of claim 1 wherein the step of de-contaminating the mold parts includes heating the parts in an inert gas furnace.

4. A molten metal sampler for measuring carbon in a low carbon melt comprising means defining a sample cavity, fill tube means communicating with said sample cavity for obtaining and conveying a sample of molten metal to said sample cavity, insulative means for supporting said sample cavity means, the improvement comprising cap means for said fill tube for preventing the entry of molten metal into said fill tube for a predetermined length of time and to prevent contaminants from entering said mold cavity, said cap means being constructed of a fusible or meltable material with low carbon content close to the carbon content of the bath being measured, elongated wall portion extending from said tip and sealing means for securing said cap to said fill tube at a joint remote from the free end of said fill tube and carbon free cement for sealing said cap at said joint.

5. A sampler in accordance with claim 4 wherein said cap means includes a cap.

6. The improvement of claim 5 wherein said cap means is made from Pyrex glass.

7. Improvement of claim 4 including an outer metal cap means surrounding said inner cap and said outer cap being a low carbon metal to match the carbon content of the steel being measured so that contamination by said outer cap when melted does not distort the representative character of the sample.

8. Improvement of claim 4 wherein said insulative means for supporting the sample mold means is refractory fiber and includes a carbon free zirconium oxide coating over a substantial portion of said refractory fiber adjacent said fill tube to prevent carbon contamination from the refractory fiber insulating means.

9. The improvement of claim 4 wherein said insulative means is made from rice hulls.

10. The improvement of claim 4 wherein said fill tube is preheated before assembly to remove contaminants.

11. The improvement of claim 4 wherein the means defining the mold cavity are metal and are pretreated to eliminate contaminants.

12. The improvement of claim 4 wherein said inner cap is mounted in substantially abutting relationship to the end of said fill tube to prevent the entry of contaminants.

13. The method of obtaining an accurate low carbon reading for molten metal comprising the steps of providing an essentially carbon free sampler with contaminant free immersion vehicle means defining a sample cavity and a contaminant free fill tube with a low carbon non-metallic cap for the fill tube and a non-carbon insulative jacket surrounding said fill tube.

* * * * *